United States Patent [19]

Grollier et al.

[11] Patent Number: 5,135,544
[45] Date of Patent: Aug. 4, 1992

[54] PROCESS FOR DYEING KERATINOUS FIBRES BASED ON MONOHYDROXYINDOLE AND 5,6-DISUBSTITUTED HYDROXYINDOLE AND COMPOSITION EMPLOYED

[75] Inventors: Jean F. Grollier, Paris; Jean Cotteret, Verneuil-sur-Seine, both of France

[73] Assignee: L'Oreal, Paris, France

[21] Appl. No.: 545,558

[22] Filed: Jun. 29, 1990

[30] Foreign Application Priority Data

Jul. 3, 1989 [FR] France .................. 89 08916

[51] Int. Cl.$^5$ .................. A61K 7/13
[52] U.S. Cl. .................. 8/405; 8/406; 8/408; 8/423; 8/424; 8/634; 424/70
[58] Field of Search .................. 8/408, 423, 424, 634, 8/405, 406; 424/70

[56] References Cited

U.S. PATENT DOCUMENTS

| | | | |
|---|---|---|---|
| 4,021,538 | 5/1977 | Yu et al. .................. | 8/10.2 |
| 4,746,322 | 5/1988 | Herlihy . | |
| 4,932,977 | 6/1990 | Schultz .................. | 8/408 |
| 5,034,015 | 7/1991 | Junino et al. .................. | 8/405 |

FOREIGN PATENT DOCUMENTS

| | | |
|---|---|---|
| 0271186 | 6/1988 | European Pat. Off. . |
| 0348280 | 12/1989 | European Pat. Off. . |
| 3031709 | 8/1980 | Fed. Rep. of Germany . |
| 2536993 | 6/1984 | France . |
| 2185498 | 7/1987 | United Kingdom . |

Primary Examiner—A. Lionel Clingman
Assistant Examiner—William S. Parks
Attorney, Agent, or Firm—Cushman, Darby & Cushman

[57] ABSTRACT

The invention relates to a process for dyeing keratinous fibres, comprising the application on these fibres, in a first stage, of a composition (A) containing, in a medium suitable for dyeing:

(i) at least one monohydroxyindole corresponding to the formula (I):

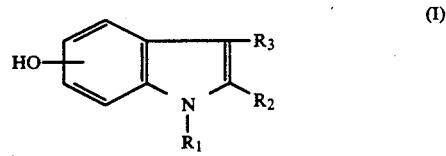

in which:
$R_1$ denotes hydrogen or alkyl; and
$R_2$ and $R_3$ denote hydrogen, $NH_2$, OH, COOH, $CH_2COOH$, $CONH_2$, alkyl optionally substituted with OH or $NH_2$, alkoxy, $CONHR_4$, $CON(R_5)(R_6)$ or $CO_2R_4$, in which $R_4$, $R_5$ and $R_6$ denote alkyl; halogen, and (ii) at least one 5,6-disubstituted hydroxyindole of formula (II):

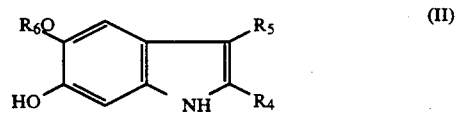

in which:
$R_6$ denotes hydrogen or acetyl;
$R_4$ denotes hydrogen, methyl, carboxy or ethoxycarbonyl; and
$R_5$ denotes hydrogen or methyl,
with the proviso that, when $R_6$ denotes acetyl, $R_4$ and $R_5$ represent a hydrogen atom; and its salts;
in a second stage, a rinsing of the treated fibres is performed; and
in a third stage, a composition (B) containing periodic acid or one of its salts in an aqueous medium is applied.

17 Claims, No Drawings

PROCESS FOR DYEING KERATINOUS FIBRES BASED ON MONOHYDROXYINDOLE AND 5,6-DISUBSTITUTED HYDROXYINDOLE AND COMPOSITION EMPLOYED

The present invention relates to a process for dyeing keratinous fibres and especially hair, employing monohydroxyindoles in combination with one or more 5,6-disubstituted hydroxyindole(s) and an oxidizing agent consisting of periodic acid, optionally salified.

It has already been proposed to dye hair or skin using monohydroxyindoles containing the hydroxyl group at the 4-, 5-, 6- and/or 7-position, employing various oxidizing agents including, in particular, periodic acid and insoluble salts.

Such a process is described, in particular, in EP-A-0,271,186.

Compositions containing 5,6-dihydroxyindole at a preferably acid pH have also been proposed for the dyeing of living hair, the application of these compositions being followed by the application of an oxidizing agent consisting, in particular, of a periodate.

Such a process is described more especially in FR-A-1,166,172, but it leads to grey to black hues not covering the whole of the desired range of hues.

These processes of the prior art have, however, the drawback of giving rise to very selective colorations, in particular when the hair has been sensitized by a permanent waving. A large difference in the dyeing power between the non-sensitized parts and those sensitized by the permanent waving is, in effect, noted in this case.

Moreover, these processes often lead to problems of staining of the scalp.

The Applicant discovered, surprisingly, that by combining one or more particular monohydroxyindole(s) with one or more 5,6-disubstituted hydroxyindole(s) defined below, this application being followed by a rinse and then by the application of a composition containing, by way of an oxidizing agent, periodic acid or one or its water-soluble salts, miscellaneous colorations were obtained, especially on hair sensitized by permanent waving, these colorations showing especially little selectivity, withstanding successive washes, exhibiting good binding and not staining the scalp.

The subject of the invention hence consists of the multi-step dyeing process comprising the application of at least one monohydroxyindole and of a 5,6-disubstituted hydroxyindole defined below, followed, after rinsing, by that of periodic acid or a salt of this acid.

The subject of the invention is finally a multicompartment device, or dyeing kit, containing the different compositions useable in the process according to the invention.

Other subjects of the invention will become apparent on reading the description and the examples which follow.

The process for dyeing keratinous fibres, especially human hair, is essentially characterized in that there is applied, in a first stage, a composition (A) containing, in a medium suitable for dyeing, (i) at least one monohydroxyindole of formula:

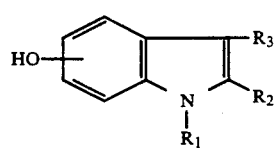

in which:
$R_1$ denotes hydrogen or an alkyl radical having 1 to 4 carbon atoms; and
$R_2$, and $R_3$ denote, independently of one another, hydrogen; an $NH_2$, OH, COOH, $CH_2COOH$ or $CONH_2$ group; an alkyl radical having 1 to 4 carbon atoms, optionally substituted with one or more OH or $NH_2$ groups; an alkoxy radical having 1 to 4 carbon atoms; a group $CONHR_4$, a group $CON(R_5)(R_6)$ or a group $CO_2R_4$, in which $R_4$, $R_5$, and $R_6$ denote an alkyl radical having 1 to 4 carbon atoms; or a halogen atom, and (ii) at least one 5,6-disubstituted hydroxyindole of formula (II), or mixture(s) thereof;

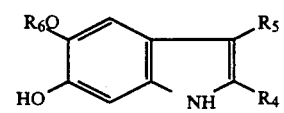

in which:
$R_6$ denotes hydrogen or acetyl;
$R_4$ denotes hydrogen, methyl, carboxy or ethoxycarbonyl; and
$R_5$ denotes hydrogen or methyl, with the proviso that, when $R_6$ denotes acetyl, $R_4$ and $R_5$ represent a hydrogen atom; and its salts;
in that, in a second stage, a rinsing of the keratinous fibres thus treated is performed, and
in that, in a third stage, a composition (B) containing, in an aqueous medium suitable for dyeing, periodic acid or one of its salts soluble in the aqueous medium is applied.

Among the compounds of formula (I), there may be mentioned:
4-hydroxyindole
5-hydroxyindole
6-hydroxyindole
7-hydroxyindole
5-hydroxy-2-indolecarboxylic acid
5-hydroxy-3-indoleacetic acid
5-hydroxy-3-hydroxyethylindole
5-hydroxy-2-hydroxymethylindole.

Among these compounds, preferred compounds consist of 5-hydroxyindole, 4-hydroxyindole, 6-hydroxyindole and 7-hydroxyindole.

Among the compounds of formula (II), there may be mentioned 5,6-dihydroxyindole, 5,6-dihydroxy-2-carboxyindole, 5,6-dihydroxy-2-ethoxycarbonylindole, 5-acetoxy-6-hydroxyinodole, 2,3-dimethyl-5,6-hydroxyindole and 2-methyl-5,6-dihydroxyindole. 5,6-Dihydroxyindole is especially preferred.

In the composition (A), the compound(s) of formula (II) and the monohydroxyindole(s) of formula (I) are present in concentrations sufficient to obtain, after application of the composition based on optionally salified periodic acid, a coloration on the keratinous fibres and especially on the hair. The concentrations of each of them are preferably between 0.01 and 5% by weight, and especially between 0.05 and 3% by weight, relative to the total weight of the composition.

Useable periodic acid salts are the water-soluble salts such as the lithium, sodium, potassium, rubidium, caesium, magnesium, calcium, strontium, manganese, iron, copper, zinc and aluminium salts, the sodium and potassium salts being especially preferred.

Periodic acid, optionally salified, is present in concentrations sufficient to oxidize the compounds of formula (I) and formula (II). These proportions are preferably between 0.004 and 0.07 mole, and especially between 0.01 mole and 0.04 mole, per 100 g of composition of optionally salified periodic acid.

According to the invention, the composition (A) is maintained in contact with the hair for an exposure time of between 1 minute and 60 minutes, and preferably between 10 minutes and 40 minutes, before being subjected to rinsing. Similarly, the composition (B) containing periodic acid or its salts is maintained in contact with the hair for an exposure time of between 1 minute and 60 minutes, and preferably between 10 minutes and 40 minutes, before the hair is rinsed and optionally washed.

The exposure times of the compositions (A) and (B) may be equal or different.

The compositions used according to the invention may be presented in various forms customarily used in the field of dyeing keratinous fibres, and in particular hair, and especially in the form of liquids, more or less thickened, creams, foams, emulsions, gels and oils.

The compositions (A) and (B) employed according to the invention generally contain an aqueous medium consisting of water or a water/solvent(s) mixture. The composition (A) can also consist of an anhydrous solvent medium which is mixed at the time of use with an aqueous medium or which is applied directly on the wet fibres.

"Anhydrous medium⇌" denotes a medium containing less than 1% of water.

Solvents useable according to the invention are selected from aliphatic alcohols such as ethyl alcohol, propyl or isopropyl alcohol or tert-butyl alcohol; polyols such as ethylene glycol, diethylene glycol, propylene glycol, glycerol or dipropylene glycol; ethylene glycol, diethylene glycol, propylene glycol or dipropylene glycol monomethyl, monoethyl or monobutyl ethers; ethylene glycol monomethyl ether acetate; and methyl lactate. The proportion of solvents can preferably vary between 1 and 50% by weight relative to the total weight of each composition.

The compositions can contain anionic, cationic, nonionic or amphoteric surfactants or mixtures thereof, in a total content preferably of between 0.5 and 20% by weight relative to the total weight of the composition.

They can also contain thickening agents such as sodium alginate, gum arabic, guar gum and its derivatives, cellulose derivatives, xanthan gum, scleroglucans, polymers derived from acrylic acid and bentonite.

The proportions of thickening agents can vary between 0.1 and 5% relative to the total weight of each composition.

When the composition (A) is aqueous, its pH is preferably between 3 and 10, and especially between 4 and 7.

The pH of the composition (B) is preferably between 2 and 10, and especially between 2.5 and 5.

The compositions employed in the process according to the invention can also contain other adjuvants customarily used in the dyeing of keratinous fibres, such as sequestering agents, antioxidant or reducing agents, film-forming agents, pearlescent agents, dispersant agents, treatment agents, fragrances, buffers, electrolytes, penetrating agents, and the like.

If the compositions are used in the form of a foam, they may be packaged under pressure in an aerosol device in the presence of a propellent agent and at least one foam-generating agent.

The process according to the invention may be employed for dyeing all types of hair, but also for dyeing furs or wool.

Another subject of the invention consists of a composition containing a plurality of separate components, comprising a first component (A) consisting of the composition (A) defined above and containing at least one monohydroxyindole as defined by the formula (I) and at least one 5,6-disubstituted hydroxyindole of formula (II) in an acceptable medium, and a component (B) consisting of the composition (B) containing periodic acid or its water-soluble salts in an acceptable medium.

The subject of the invention is also a dyeing kit or multi-compartment device, comprising a first compartment containing the composition (A) defined above, and a second compartment containing the composition (B) also defined above. This device can optionally contain a third compartment containing an aqueous medium designed to be mixed with the contents of the first compartment when the medium used for the composition (A) is anhydrous.

The examples which follow are designed to illustrate the invention, no limitation of the latter being, however, implied.

EXAMPLE 1

| Composition (A): | |
|---|---|
| 5,6-Dihydroxyindole | 0.4 g |
| 5-Hydroxyindole | 0.6 g |
| Ethyl alcohol | 10.0 g |
| Guar gum sold by the company CELANESE under the name JAGUAR HP60 | 1.0 g |
| Glycoside alkyl ether sold at a concentration of 60% AS by the company SEPPIC under the name TRITON CG 110 | 5.0 g AS |
| Preservatives qs | |
| Adjusted pH | between 6.5 and 6.9 |
| Demineralized water | qs 100.0 g |
| Composition (B): | |
| Sodium metaperiodate | 5.0 g |
| HCl qs pH 3 | |
| Demineralized water | qs 100.0 g |

The composition (A) is applied on grey hair which is 90% white. After 15 minutes' exposure, the hair is rinsed. The composition (B) is then applied for 15 minutes. The hair is rinsed again and dried. The hair is then dyed in a deep blond hue. This hue shows little selectivity on permanent waving.

EXAMPLE 2

The 0.6 g of 5-hydroxyindole of the composition (A) of Example 1 is replaced by 0.6 g of 6-hydroxyindole. A light brown hue showing little selectivity on permanent waving is finally obtained.

EXAMPLE 3

The 0.6 g of 5-hydroxyindole of the composition (A) of Example 1 is replaced by 0.6 g of 4-hydroxyindole. An ash brown hue showing little selectivity on permanent waving is finally obtained.

EXAMPLE 4

The 0.6 g of 5-hydroxyindole of the composition (A) of Example 1 is replaced by 0.6 g of 7-hydroxyindole. A purple-violet dark auburn-coloured light brown hue showing little selectivity on permanent waving is finally obtained.

EXAMPLE 5

| Composition (A): | |
|---|---|
| 5,6-Dihydroxyindole | 0.2 g |
| 6-Hydroxyindole | 0.4 g |
| Ethyl alcohol | 10.0 g |
| Guar gum sold by the company CELANESE under the name JAGUAR HP 60 | 1.0 g |
| Glycoside alkyl ether sold at a concentration of 60% AS by the company SEPPIC under the name TRITON CG 110 | 5.0 g AS |
| Adjusted pH | between 6.5 and 6.9 |
| Preservatives qs | |
| Water | qs 100.0 g |

The composition (A) is applied for 15 min on grey hair which is 90% white. The hair is rinsed. The composition (B) described in Example 1 is then applied for 15 min. The hair is rinsed and dried. The hair is dyed in an ash blond hue showing little selectivity on permanent waving.

EXAMPLE 6

Example 1 is reproduced, with 0.1 g of 5,6-dihydroxyindole instead of 0.4 g and replacing the 0.6 g of 5-hydroxyindole by 0.25 g of 4-hydroxyindole; the hue obtained is uniform medium grey; it shows little selectivity on permanent waving.

EXAMPLE 7

Example 1 is reproduced, with 0.1 g of 5,6-dihydroxyindole instead of 0.4 g and replacing the 0.6 g of 5-hydroxyindole by 0.25 g of 7-hydroxyindole; the hue obtained is dark auburn-coloured deep blond; it shows little selectivity on permanent waving. For the different examples mentioned above, a substantial decrease was observed in the selectivity as a result of the combination, this substantial decrease in selectivity being observed by determining the colour in the MUNSELL system, on natural grey hair on the one hand, and on permanent-waved grey hair on the other hand.

It is found that the difference in colour between these two types of hair, determined according to NICKERSON's formula: $\Delta E = 0.4 C_o dH + 6 dV + 3 dC$ defined Journal of the Optical Society of America, Volume 34, No. 9, September 1944, pages 550 to 570, is substantially smaller in the case of the process of the invention.

In this equation, $\Delta E$ represents the total colour variation and dH, dV and dC represent the variations, as an absolute value, of the MUNSELL parameters H, V and C, $C_o$ being the chromaticity of the initial colour.

EXAMPLE 8

| Composition (A): | |
|---|---|
| 5-Hydroxyindole | 0.5 g |
| 5,6-Dihydroxyindole | 0.3 g |
| 2,3-Dimethyl-5,6-dihydroxyindole hydrobromide | 0.3 g |
| Ethyl alcohol | 10.0 g |
| Hydroxyethylcellulose sold by the company AQUALON under the name NATROSOL 250 HHR | 0.5 g |
| Sodium lauryl ether sulphate | 0.1 g AS |
| Triethanolamine qs pH 6.5 | |
| Water | qs 100.0 g |

The composition (A) is applied for 15 minutes on grey hair which is 90% white. The hair is rinsed.

The composition (B) described in Example 1 is then applied for 15 minutes. After rinsing, washing with shampoo and drying, the hair is dyed a dark auburn-coloured natural deep brown.

EXAMPLE 9

| Composition (A): | |
|---|---|
| 6-Hydroxyindole | 0.5 g |
| 5,6-Dihydroxy-2-ethoxycarbonylindole | 0.5 g |
| Ethyl alcohol | 10.0 g |
| Hydroxyethylcellulose sold by the company AQUALON under the name NATROSOL 250 HHR | 0.5 g |
| Sodium lauryl ether sulphate | 0.1 g AS |
| Triethanolamine qs pH 6.5 | |
| Water | qs 100.0 g |

The composition (A) is applied for 30 minutes on grey hair which is 90% white. The hair is rinsed.

The composition (B) described in Example 1 is then applied for 15 minutes. After rinsing, washing with shampoo and drying, the hair is dyed a golden natural brown.

EXAMPLE 10

| Composition (A): | |
|---|---|
| 7-Hydroxyindole | 0.2 g |
| 5,6-Dihydroxyindole | 0.1 g |
| 2-Methyl-5,6-dihydroxyindole hydrobromide | 0.5 g |
| Ethyl alcohol | 10.0 g |
| Hydroxyethylcellulose sold by the company AQUALON under the name NATROSOL 250 HHR | 0.5 g |
| Sodium lauryl ether sulphate | 0.1 g AS |
| Triethanolamine qs pH 6.5 | |
| Water | qs 100.0 g |

The composition (A) is applied for 15 minutes on permanent-waved grey hair. The hair is rinsed.

The composition (B) described in Example 1 is then applied for 30 minutes. After rinsing, washing with shampoo and drying, the hair is dyed a dark auburn-coloured deep brown.

EXAMPLE 11

| Composition (A): | |
|---|---|
| 6-Hydroxyindole | 0.2 g |
| 5,6-Dihydroxyindole | 0.4 g |
| 5,6-Dihydroxy-2-carboxyindole | 0.4 g |
| Hydroxyethylcellulose sold by the company AQUALON under the name NATROSOL 250 HHR | 1.0 g |
| Ethyl alcohol | 10.0 g |
| Sodium lauryl ether sulphate | 0.2 g |

| -continued | |
|---|---|
| Triethanolamine qs pH 6.5 | |
| Water | qs 100.0 g |
| Composition (B): | |
| Sodium metaperiodate | 2.5 g |
| HCl qs pH 3 | |
| Water | qs 100.0 g |

The composition (A) is applied for 15 minutes on permanent-waved grey hair. The hair is rinsed.

The composition (B) is then applied for 15 minutes. After rinsing, washing with shampoo and drying, the hair is dyed brown.

EXAMPLE 12

| Composition (A): | |
|---|---|
| 5-Hydroxyindole | 0.3 g |
| 5,6-Dihydroxyindole | 0.1 g |
| 5-Acetoxy-6-hydroxyindole | 0.3 g |
| Hydroxyethylcellulose sold by the company AQUALON under the name NATROSOL 250 HHR | 1.0 g |
| Ethyl alcohol | 10.0 g |
| Sodium lauryl ether sulphate | 0.2 g |
| Triethanolamine qs pH 6.5 | |
| Water | qs 100.0 g |

The composition (A) is applied for 15 minutes on grey hair which is 90% white. The hair is rinsed.

The composition (B) described in Example 11 is then applied for 15 minutes. After rinsing, washing with shampoo and drying, the hair is dyed an iridescent light brown.

EXAMPLE 13

| Composition (A): | |
|---|---|
| 5-Hydroxyindole | 0.05 g |
| 5,6-Dihydroxyindole | 3.5 g |
| Hydroxyethylcellulose sold by the company AQUALON under the name NATROSOL 250 HHR | 1.0 g |
| Ethyl alcohol | 10.0 g |
| Sodium lauryl ether sulphate | 0.2 g AS |
| Triethanolamine qs pH 6.5 | |
| Water | qs 100.0 g |

The composition (A) is applied for 15 minutes on grey hair which is 90% white. The hair is rinsed.

The composition (B) described in Example 11 is then applied for 15 minutes. After rinsing, washing with shampoo and drying, the hair is dyed brown.

We claim:

1. A process for dyeing keratinous fibers comprising applying to said fibers, in a first stage, a composition (A) containing in a medium suitable for dyeing said fibers
    (ii) at least one monohydroxyindole having the formula

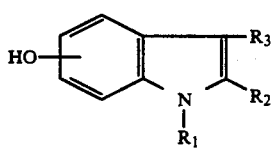

wherein
$R_1$ represents hydrogen or $C_1$-$C_4$ alkyl,
$R_2$ and $R_3$, each independently, represent hydrogen, $NH_2$, OH COOH, $CH_2COOH$, $CONH_2$, $C_1$-$C_4$ alkyl, $C_1$-$C_4$ alkyl substituted with one or more OH or $NH_2$ groups, alkoxy having 1–4 carbon atoms, $CONHR_4$, $CON(R_5)$ ($R_6$) or $CO_2R_4$ wherein $R_4$, $R_5$ and $R_6$ represent alkyl having 1–4 carbon atoms or halogen, said monohydroxyindole being present in an amount ranging from 0.01 to 5 percent by weight based on the total weight of said composition (A), and
    (ii) at least one 5, 6-disubstituted hydroxyindole or a mixture thereof having the formula

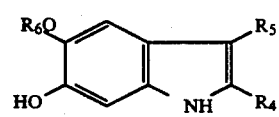

wherein
$R_6$ represents hydrogen or acetyl,
$R_4$ represents hydrogen, methyl, carboxy or ethoxy carbonyl and
$R_5$ represents hydrogen or methyl,
with the proviso that when $R_6$ represents acetyl, $R_4$ and $R_5$ represent hydrogen,
and a salt thereof,
said 5,6-disubstituted hydroxyindole being present in an amount ranging from 0.01 to 5 percent by weight based on the total weight of said composition (A),
in a second stage rinsing said fibers treated with said composition (A) in said first stage and
in a third stage, applying to said rinsed fibers a composition (B) containing in an aqueous medium suitable for dyeing said fibers a periodic acid or a salt thereof soluble in said aqueous medium, said periodic acid or salt thereof being present in an amount ranging from 0.004 to 0.07 mole per 100 g of said composition (B).

2. The process of claim 1 wherein said monohydroxyindole is selected from the group consisting of
    4-hydroxyindole,
    5-hydroxyindole,
    6-hydroxyindole,
    7-hydroxyindole,
    5-hydroxy-2-indole carboxylic acid,
    5-hydroxy-3-indole acetic acid,
    5-hydroxy-3-hydroxyethylindole and
    5-hydroxy-2-hydroxymethylindole.

3. The process of claim 1 wherein said 5,6-disubstituted hydroxyindole of formula (II) is 5,6-dihydroxyindole.

4. The process of claim 1 wherein said 5,6-disubstituted hydroxyindole of formula (II) is selected from the group consisting of
    5,6-dihydroxy-2-carboxyindole,
    5,6-dihydroxy-2-ethoxycarbonylindole,
    5-acetoxy-6-hydroxyindole,
    2,3-dimethyl-5,6-dihydroxyindole and
    2-methyl-5,6-dihydroxyindole.

5. A process for dying keratinous fibers comprising applying to said fibers, in a first stage, a composition (A) containing, in a medium suitable for dyeing said fibers,
    (i) at least one monohydroxyindole selected from the group consisting of 4-hydroxyindole, 6-hydroxyindole and 7-hydroxyindole present in an amount ranging from 0.01 to 5 percent by weight based on the total weight of said composition (A) and (ii) at least one 5,6-dihydroxyindole present in an amount ranging from 0.01 to 5 percent by weight based on the total weight of said composition (A), in a second stage, rinsing said fibers treated in said first stage and in a third stage, applying to said rinsed fibers a composition (B) containing in an aqueous medium, suitable for dyeing said fibers, periodic acid or a salt thereof soluble in said aqueous medium, said periodic acid or salt thereof being present in an amount ranging from 0.004 to 0.07 mole per 100 g of said composition (B).

6. The process of claim 1 wherein said salt of periodic acid is the lithium, sodium, potassium, rubidium, caseium, magnesium, calcium, strontium, manganese, iron, copper, zinc and aluminum salt thereof.

7. The process of claim 1 wherein said composition (A) is permitted to remain in contact with said fibers for a period of time ranging from 1 to 60 minutes prior to rinsing said fibers and said composition (B) is permitted to remain in contact with said fibers for a period of time ranging from 1 to 60 minutes, the contact time of said compositions (A) and (B) being identical or different.

8. The process of claim 1 wherein the medium for said composition (A) and the aqueous medium for said composition (B) are water or a water/solvent mixture.

9. The process of claim 1 wherein the medium for said composition (A) is an anhydrous solvent.

10. The process of claim 8 wherein said solvent is an aliphatic alcohol, a polyol, ethylene glycol, diethylene glycol, propylene glycol, dipropylene glycol monomethyl ether, dipropylene glycol monoethyl ether, dipropylene glycol monobutyl ether, ethylene glycol monomethyl ether acetate and methyl lactate.

11. The process of claim 1 wherein said medium for composition (A) is an aqueous medium and said composition (A) has a pH ranging from 3 to 10.

12. The process of claim 1 wherein said medium for composition (A) is an aqueous medium and said composition (A) has a pH ranging from 4 to 7.

13. The process of claim 1 wherein said composition (B) has a pH ranging from 2 to 10.

14. The process of claim 1 wherein each of said compositions (A) and (B) contains a thickening agent present in an amount ranging from 0.1 to 5 percent by weight based on the total weight of said composition.

15. The process of claim 1 wherein the medium for one or both of said composition (A) and (B) also contains at least one of a surfactant, a sequestering agent, an antioxidant, a reducing agent, a film forming agent, a pearlescent agent, a dispersant agent, a treatment agent, a penetrating agent, a fragrance, a buffer and an electrolyte.

16. A dyeing agent comprising a first component comprising a composition (A) containing in a cosmetically acceptable medium at least one monohydroxyindole having the formula

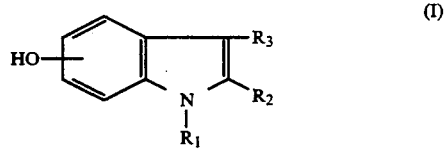

$R_1$ represents hydrogen or alkyl containing 1-4 carbon atoms, and $R_2$ and $R_3$, each independently, represent hydrogen, $NH_2$, OH, COOH, $CH_2COOH$, $CONH_2$, $C_1-C_4$ alkyl, alkyl having 1-4 carbon atoms and substituted with one or more OH or $NH_2$ groups, alkoxy having 1-4 carbon atoms, $CONHR_4$, $CON(R_5)(R_6)$, or $CO_2R_4$ wherein $R_4$, $R_5$, $R_6$ represent alkyl having 1-4 carbon atoms or halogen, said monohydroxyindole being present in an amount ranging from 0.01 to 5 percent by weight based on the total weight of said composition (A), and at least one 5,6-disubstituted hydroxyindole having the formula

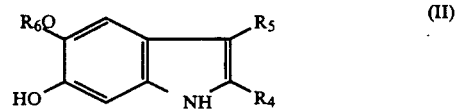

wherein $R_6$ represents hydrogen or acetyl, $R_4$ represents hydrogen, methyl, carboxy or ethoxy carbonyl and $R_5$ represents hydrogen or methyl, with the proviso that when $R_6$ represents acetyl, $R_4$ and $R_5$ represent hydrogen, and a salt thereof, said 5,6-disubstituted hydroxyindole being present in an amount ranging from 0.01 to 5 percent by weight based on the total weight of said composition (A); and a second component comprising in a medium suitable for dyeing, a composition (B) containing periodic acid or a watersoluble salt thereof, said periodic acid or salt thereof being present in an amount ranging from 0.004 to 0.07 mole per 100 g of said composition (B).

17. The dyeing agent of claim 16 in the form of a multicompartment device or kit comprising a first compartment containing said composition (A) and a second compartment containing said composition (B).

* * * * *